(12) United States Patent
Kluczynski et al.

(10) Patent No.: US 8,094,313 B2
(45) Date of Patent: Jan. 10, 2012

(54) WAVELENGTH MODULATION SPECTROSCOPY METHOD AND SYSTEM

(75) Inventors: Pawel Kluczynski, Västra Frölunda (SE); Stefan Lundqvist, Askim (SE); Per-Arne Thorsén, Öjersjö (SE)

(73) Assignee: Siemens Aktiengesellschaft, Munich (DE)

( * ) Notice: Subject to any disclaimer, the term of this patent is extended or adjusted under 35 U.S.C. 154(b) by 428 days.

(21) Appl. No.: 12/317,059

(22) Filed: Dec. 18, 2008

(65) Prior Publication Data

US 2009/0201507 A1    Aug. 13, 2009

(30) Foreign Application Priority Data

Dec. 21, 2007    (EP) .................................. 07024934

(51) Int. Cl.
*G01N 21/00*    (2006.01)

(52) U.S. Cl. ...................................... 356/437

(58) Field of Classification Search ........................ None
See application file for complete search history.

(56) References Cited

U.S. PATENT DOCUMENTS

| | | | |
|---|---|---|---|
| 4,945,234 A * | 7/1990 | Goodman et al. | 250/291 |
| 5,173,749 A | 12/1992 | Tell et al. | |
| 6,356,350 B1 | 3/2002 | Silver et al. | |
| 6,611,335 B1 * | 8/2003 | Hovde | 356/437 |
| 7,116,422 B2 | 10/2006 | Larking et al. | |
| 7,230,711 B1 * | 6/2007 | Hovde | 356/432 |
| 2005/0140979 A1 | 6/2005 | Kluczynski et al. | |
| 2008/0221814 A1 * | 9/2008 | Trainer | 356/338 |

FOREIGN PATENT DOCUMENTS

EP    1510798 A1    3/2005

OTHER PUBLICATIONS

Gurlit et al.; "Lightweight diode laser spectrometer CHILD, (Compact High-altitude In-situ Laser Diode) for balloon borne measurements of water vapor and methane", Applied Optics, vol. 44, No. 1, pp. 91-102, Jan. 2005.

Durry et al.; "Atmospheric CH4 and H2O monitoring with near-infrared InGaAs laser diodes by the SDLA, a balloonborne spectrometer for tropospheric and stratospheric in situ measurements", Applied Optics, vol. 38 No. 36, pp. 7342-7354, Dec. 1999.

(Continued)

*Primary Examiner* — Gregory J Toatley
*Assistant Examiner* — Juan D Valentin

(57) ABSTRACT

A method and system for measuring the concentration of a gas component in a measuring gas a provided. The wavelength of a light source is modulated with a modulation signal at a modulation frequency, while the wavelength is swept over an interaction feature of a sample. The intensity of the light source is further modulated at a wavelength outside the interaction feature with a burst signal, where an N-th harmonic of the burst frequency coincides with an M-th harmonic of the modulation frequency. The light is passed to the sample and thereafter to a detector. The detector output is demodulated at the M-th harmonic, and the demodulated detector output is normalized by calculating the ratio between a demodulated detector output portion derived from the light modulated with the modulation signal and another demodulated detector output portion derived from the light modulated with the burst signal.

19 Claims, 2 Drawing Sheets

OTHER PUBLICATIONS

Scott et al; "Airborne Laser Infrared Absorption Spectrometer (ALIAS-II) for in situ atmospheric measurements of $N_2O$, $CH_4$, CO, HCl and $NO_2$ from balloon or remotely piloted aircraft platforms", Applied Optics, vol. 38, No. 21, pp. 4609-4622, Jul. 1999.

Kluczynski et al. ; "Theoretical description based on Fourier analysis of wavelength-modulation spectrometry in terms of analytical and background signals", Applied Optics, vol. 38, No. 27, pp. 5803-5815, Sep. 1999.

* cited by examiner

WAVELENGTH MODULATION SPECTROSCOPY METHOD AND SYSTEM

CROSS REFERENCE TO RELATED APPLICATIONS

This application claims priority of European Patent Office application No. 0702493.7 EP filed Dec. 21, 2007, which is incorporated by reference herein in its entirety.

FIELD OF INVENTION

The invention relates to a wavelength modulation spectroscopy method. It further relates to a wavelength modulation spectroscopy system.

BACKGROUND OF INVENTION

In wavelength modulation spectroscopy (WMS) the wavelength of the light of a tunable light source, such as a diode laser, is modulated with a frequency $f_0$, while the wavelength is swept over a molecular absorption line of a gas component of interest in a gas sample. As the light propagates along a measurement path through the gas sample, wavelength dependent absorption converts some of the wavelength modulation into an amplitude modulation of the light. Thus, the light will have an overtone spectrum generated by the absorption, the harmonic content of the spectrum being dependent on the width and shape of the molecular absorption line in the gas and the etalons in the optical path of the measuring system. When the light then impinges onto a measuring detector, for example a photodiode, the detector output contains AC components at the modulation frequency $f_0$ and its higher harmonics $Mf_0$ (M=2, 3, 4, etc.). Demodulating the detector output at one of said higher harmonics, preferably at $2f_0$, shifts the measurement from frequencies near DC, where the light source is noisy, into a higher frequency range, where the noise is lower, thus improving the measurement sensitivity.

SUMMARY OF INVENTION

In order to measure absolute gas concentrations, a suitable normalization method is needed for compensating for general fluctuations in the emitted light intensity and non-gas related transmission in the optical path of the measuring system. For example, in in-situ measurements of trace gases in combustion environments where varying dust loads, high temperature, gas turbulences etc. modulate the light in the kHz range, it is important that the normalization is not distorted by the rapidly changing transmission and turbulences in the measurement path.

Light which propagates through weakly absorbing gases is attenuated exponentially according to the Beer-Lambert law:

$$I(v) = I_L(v)T \cdot \exp\left[-\sum_i c_i \alpha_i(v) L\right],\quad \text{(Equation 1)}$$

where I is the intensity of the light after passing through the measurement path, $I_L$ is the intensity of the light emitted from the light source, T is a transmission factor over the measurement path, which transmission factor stands for the wavelength independent transmission including optical losses, $\alpha_i$ is the absorption coefficient of a gaseous species i with the concentration $c_i$, and L is the length of the measurement path. The absorption coefficient $\alpha_i$ is dependent on the light frequency v (or the wavelength). For small optical absorption, Equation 1 reduces to:

$$I(v) = I_L(v)T\left[1 - \sum_i c_i \alpha_i(v) L\right].\quad \text{(Equation 2)}$$

As mentioned above, wavelength modulation spectroscopy utilizes a rapid modulation of the emitted light with a frequency $f_0$, while the wavelength is swept over a molecular absorption line of a gas component of interest in the gas sample. The light impinging on the detector can then be written as:

$$I(v)=I_L(v)T(1-\alpha_0\chi(v)c_0L)=I_{BG}(v)+I_{AS}(v)\quad \text{(Equation 3)}$$

[Applied Optics, Vol. 38, No. 27, pp. 5803-5815 (September 1999)], where $\alpha_0$ and $\chi$ represent the intensity and the peak-normalized shape of the molecular absorption line of interest. $I_{BG}$ and $I_{AS}$ are the background and analytical light portions, respectively, and are defined as:

$$I_{BG}(v)=I_L(v)T\quad \text{(Equation 4)}$$

$$I_{AS}(v)=-I_L(v)T\alpha_0\chi(v)c_0L\quad \text{(Equation 5)}.$$

As can be seen from Equations 4 and 5, independent measuring of the non-gas related transmission $I_LT$ is needed to measure absolute gas concentrations.

The most straight forward method to measure the non-gas related transmission $I_LT$ is to use a direct detection. The wavelength of the light is swept by a triangular or sawtooth waveform over the absorption line of the gas component to be measured wherein the beginning and the end of the scan are well separated from the absorption peak. The measuring detector output is compared with the signal from a monitor detector which directly monitors the output intensity of the light source. The direct detection channel then detects the large triangular scan as a measure of the transmitted optical power. The scan also includes a period where the light source is turned off in order to provide an accurate zero irradiance reference. [Applied Optics, Vol. 38, No. 36, pp. 7342-7354 (December 1999) and Applied Optics, Vol. 44, No. 1, pp. 91-102 (January 2005)].

In wavelength modulation spectroscopy a combination of wavelength modulation and direct detection can be used [Applied Optics, Vol. 38, No. 21, pp. 4609-4622 (July 1999)]. This technique is mostly developed for atmospheric monitoring; to be used in harsh industrial environment, the modulation rate has to be increased in order to place the signal energy above that of the turbulent measuring medium.

In wavelength modulation spectroscopy an indirect measure of the non-gas related optical transmission can be obtained by the use of the wavelength modulation signal $f_0$, which makes it necessary to introduce a separate detection channel for the fundamental frequency [U.S. Pat. No. 5,173,749]. An intentionally injected pilot tone at a higher harmonic $Mf_0$ of said wavelength modulation signal [U.S. Pat. No. 7,116,422] avoids the use of such a separate electronic channel. A drawback of this method, however, is that the received pilot tone amplitude gives only information about the transmission factor T rather than the detected non-gas related light intensity $I_LT$, thus $I_L$ has to be measured separately, e.g. by division with a reference cell signal [U.S. Pat. No. 5,173,749], which introduces the necessity of an additional optical channel. Therefore, in order to obtain $I_LT$ directly, the modulation of the light source should also include turning off the emitted light entirely.

Therefore, the invention seeks to provide a wavelength modulation spectroscopy method and system, which effectively compensate variations in the emitted light intensity and in the non-gas related transmission of the measurement path.

According to the invention this is achieved by the method and the system defined in the independent claims.

Preferred embodiments of the method and the system according to the invention are specified in the remaining claims.

According to the present invention normalization is based on a burst signal, the frequency of which lies above that of the turbulences and flame spectra in the measurement path. The burst signal waveform is optimized to maximize the intensity modulation effect while its amplitude is chosen to allow periodic interruption of the laser emission. Moreover, the burst frequency is chosen so that a suitable overtone can be detected by the same signal chain or channel as that of the analytical signal portion thereby using preferably a down sampling scheme.

BRIEF DESCRIPTION OF THE DRAWINGS

The present invention will be now described by way of example and with reference to the accompanying drawings, in which.

DETAILED DESCRIPTION OF INVENTION

Figure 1:
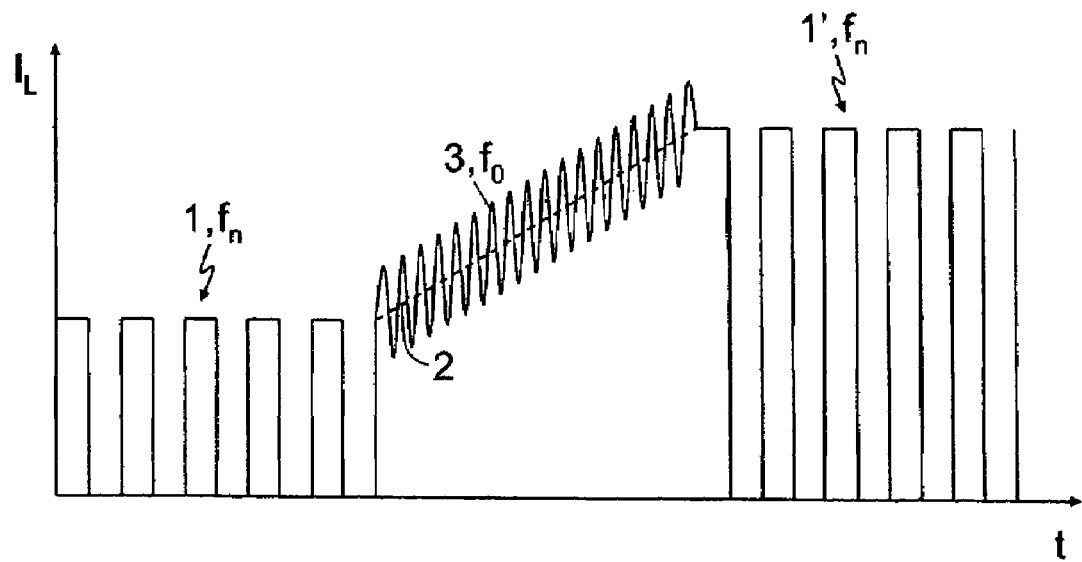
FIG. 1 shows an example for the light modulation with a burst and a sinusoidal signal.

FIG. 1 shows an example of the modulation of the intensity $I_L$ of the light emitted from a light source, preferably a diode laser. The modulation periodically alternates between a burst 1, 1' with a burst frequency $f_n$ and a triangular or sawtooth sweep function 2 with a superimposed sinusoidal modulation 3 at a modulation frequency $f_0$. The purpose of the sweep function 2 is to allow light wavelength scan across an absorption line of a gas component of interest. It is advantageous, although not necessary, to apply the burst 1, 1' with different amplitudes before and after the sweep function 2 to allow measure of the eventual changes in the optical power vs. injection current characteristics of the diode laser.

The waveform and the frequency $f_n$ of the burst 1, 1' are preferably chosen to allow a settling time of the diode laser. The optimum choice is a square wave. Furthermore, the burst frequency $f_n$ is arranged so that an N-th harmonic $Nf_n$ of the waveform coincides with an M-th harmonic $Mf_0$ of the modulation frequency $f_0$, at which M-th harmonic $Mf_0$ the analytical light portion $I_{AS}$ (cf. Equation 5) is detected. Thus, for the purpose of normalization, a suitable overtone can be detected by the same signal chain or channel as that for evaluation the analytical signal portion. The choice of harmonics M and N is also made to allow for an optimum relation in amplitude between the normalization signal and the analytical signal, thus allowing an optimum dynamic range of the single signal chain.

The M-th harmonic of the detected analytical light portion (cf. Equation 5) can be written as:

$$I_{AS,Mf_0}(t) = \alpha_0 \chi_M I_L T c_i L \cos(2\pi M f_0 t) \quad \text{(Equation 6)}$$

The detected light intensity as a result of the square wave burst modulation shown in FIG. 1 can be then written as:

$$I_{burst}(t) = I_L T \frac{2}{\pi}\left(\frac{\pi}{4} + \sum_{k=1,3,5,\ldots}^{K} (-1)^{(k+1)/2} \frac{1}{k}\cos(2\pi k f_n t)\right), \quad \text{(Equation 7)}$$

where K depends on the bandwidths of the laser driver and the detector.

As the burst frequency $f_n$ is arranged so that an N-th harmonic $Nf_n$ of the burst frequency $f_n$ coincides with an M-th harmonic $Mf_0$ of the modulation frequency $f_0$, the following relation is given:

$$f_0 = \frac{N}{M} f_n, \quad \text{(Equation 8)}$$

where N=1, 3, 5, . . . .

If another waveform configuration is used when the modulation and burst signals simultaneously, a further aspect when determining the relation between these two frequencies $f_0$ and $f_n$ is to avoid distortion due to overlap between frequency components of the measurement and burst signal. In this case the bandwidth B of the measured signal at $Mf_0$ has to fulfill the following relation:

$$B < 2f_n \quad \text{(Equation 9)}.$$

By inserting Equation 8 in Equations 6 and 7, respectively, one obtains:

$$I_{AS,Nf_n}(t) = \alpha_0 \chi_M I_L T c_i L \cos(2\pi N f_n t) \quad \text{(Equation 10)}$$

and $$I_{burst,Nf_n}(t) = I_L T \frac{2}{N\pi}(-1)^{(N+1)/2}\cos(2\pi N f_n t). \quad \text{(Equation 11)}$$

Figure 2:
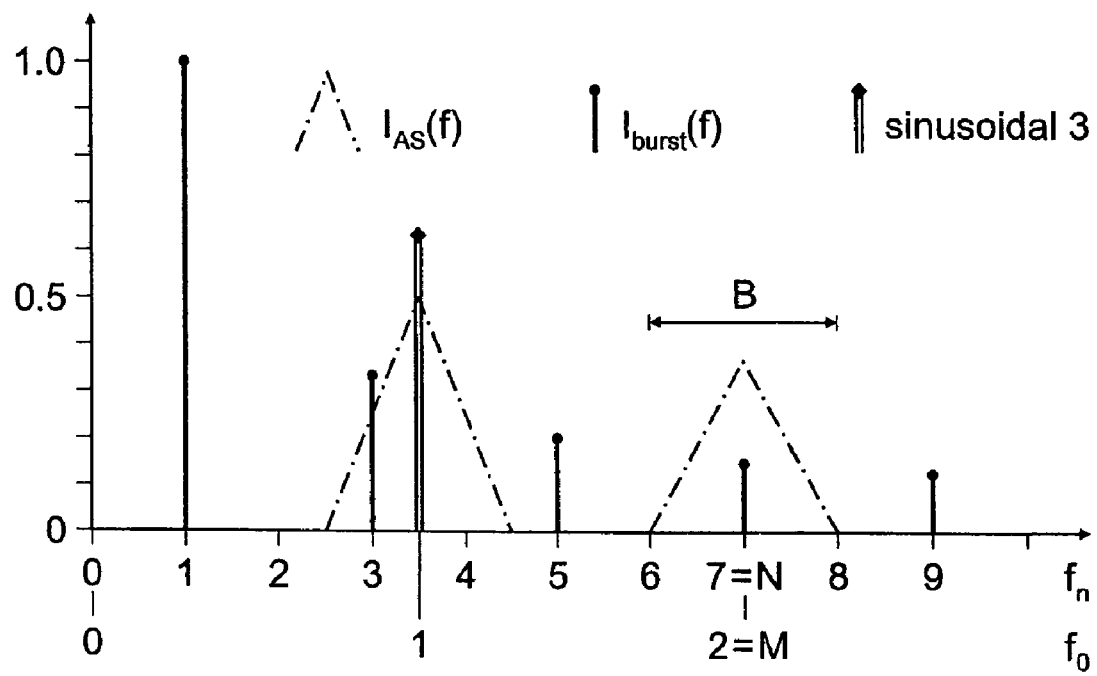
FIG. 2 shows the Fourier spectra of the detected burst and analytical signal portions.

FIG. 2 shows the Fourier spectra of the detected burst and analytical signal portions $I_{burst}(f)$ and $I_{AS}(f)$ for N=7 and M=2. The $Nf_0$ frequency components can be filtered and amplified before downsampling.

By performing downsampling at a sampling frequency $F_s=(N+1)f_n$, Equation 10 can be written as:

$$I_{AS,Nf_n}(n) = \alpha_0 \chi_M I_L T c_i L \cos\left(2\pi n \frac{N}{N+1}\right), \quad \text{(Equation 12)}$$

where n is a sample number. Similarly, Equation 11 becomes:

$$I_{burst,Nf_n}(n) = I_L T \frac{2}{N\pi}(-1)^{(N+1)/2}\cos\left(2\pi n \frac{N}{N+1}\right). \quad \text{(Equation 13)}$$

Since N/(N+1)>1/2, aliasing takes place. Reconstruction of the discrete signals given by Equations 12 and 13 gives:

$$\cos\left(2\pi n \frac{N}{N+1}\right) \xrightarrow{f_n t = n/(N+1)} \cos(2\pi f_n t). \quad \text{(Equation 14)}$$

Figure 3:
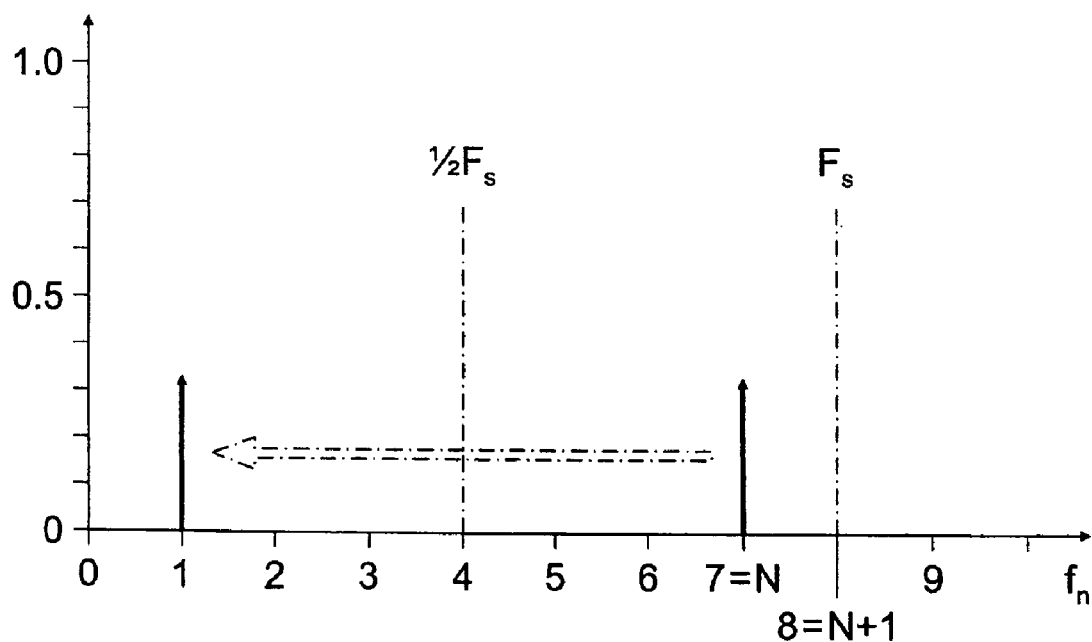
FIG. 3 illustrates the down sampling procedure.

Thus, by performing down sampling at a sampling frequency $F_s=(N+1)f_n$, the M-th harmonic of the detected analytical light portion $I_{AS,Nf_n}$ and the N-th harmonic $I_{burst,Nf_n}$ of the burst are both converted down to $f_n$ due to the aliasing effect. This effect is shown in FIG. 3.

Combination of Equations 12 and 13 yields the following formula for gas concentration:

$$c_i = \frac{2(-1)^{(N+1)/2}}{\alpha_0 \chi_M L N \pi} \cdot \frac{I_{AS,f_n}}{I_{burst,f_n}}.$$ (Equation 15)

As can be seen, the concentration $c_i$ is no longer dependent on the non-gas related optical transmission $I_L T$.

The above method is especially advantageous to utilize an audio analog-to-digital converter with a sampling frequency $F_s$=192 kHz. This avoids the necessity of an extra downsampling stage. The burst frequency is then $f_n$=24 kHz, while the modulation frequency is $f_0$=84 kHz. The $7f_n$ burst and $2f_0$ analytical signal fall both in a 168 kHz frequency band. Sampling at 192 kHz aliases the 168 kHz band back to 24 kHz where they can be easily processed further.

Figure 4:
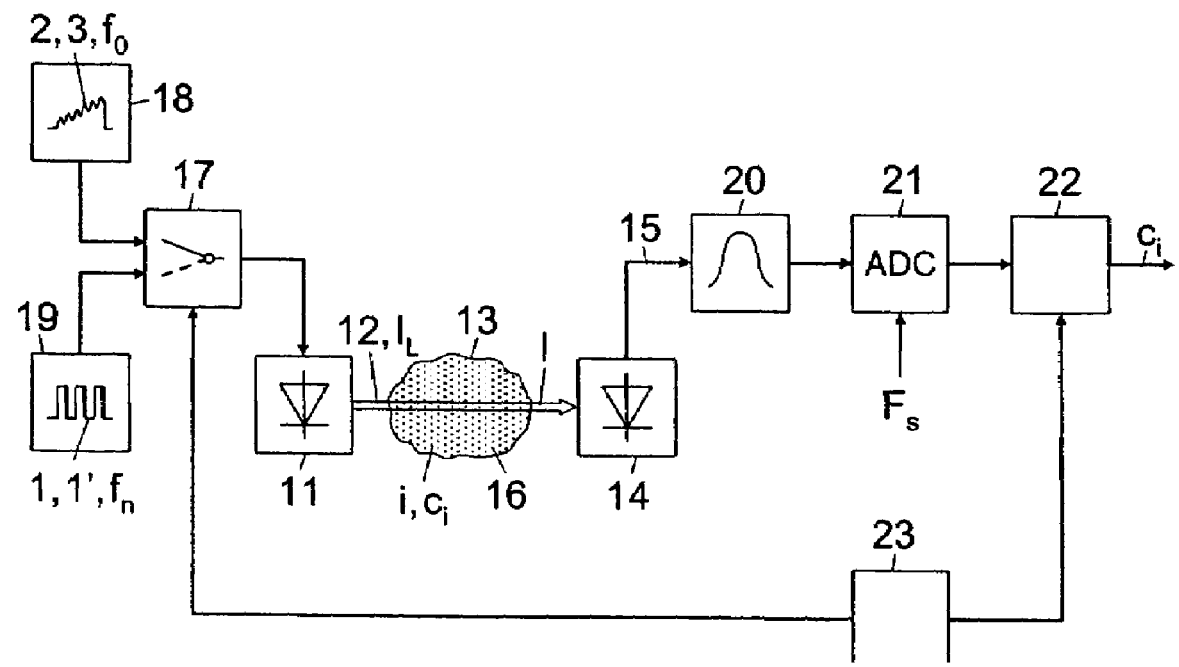
FIG. 4 is a schematic block diagram of the system in accordance with the invention.

FIG. 4 shows a wavelength modulation spectroscopy system including a frequency tunable light source 11 in form of a diode laser for generating light 12 in form of a laser beam and of intensity $I_L$ which is passed along a single optical path through a measuring volume 13 to a detector 14 for generating an output 15 indicative of the received light intensity I. The measuring volume 13, which can be a sample cell or, in case of in-situ process measurements, a gas-leading pipe, furnace, funnel or the like, contains a measuring gas (sample) 16, in which the concentration $c_i$ of a specific gas component i is to be measured. The modulation of the diode laser 11 is switched by means of a switch 17 between the sweep signal 2 with the added modulation signal 3 of the frequency $f_0$, provided by a waveform generator 18, and the burst signal 1, 1' turning on and off the diode laser 11 at frequency $f_n$, provided by a burst generator 19. The frequencies $f_0$ and $f_n$ are related such that $Mf_0=Nf_n$, where N is an integer corresponding to a suitable harmonic of the burst signal 1, 1' and M is the harmonic of the modulation frequency $f_0$ where detection of the absorption in the measuring volume 13 will be made. The generated laser light 12 is passed through the measuring volume 13 and picked up by the detector diode 14. The output 15 of the detector 14 is filtered through a band-pass filter 20 with a centre frequency $Mf_0$ and then converted to digital format in an analog-to-digital converter 21 running at a sampling frequency $F_s=(N+1)f_n$ hence causing both the M-th harmonic of $f_0$ and the N-th harmonic of $f_n$ to be folded or aliased back to frequency $f_n$. The down-converted detector output is then processed by the digital signal processing unit 22 for calculating the concentration $c_i$ of the specific gas component i to be measured. Due to a synchronisation unit 21 the signal processing unit 22 can separate the parts of the detector output related to modulation generated by the burst generator 19 at the burst frequency $f_n$ from those parts related to modulation by the waveform generator 18 at the modulation frequency $f_0$.

The invention claimed is:

1. A wavelength modulation spectroscopy method comprising:
    periodically sweeping a wavelength of a beam of light from a light source according to a sweep function;
    directing the beam of light through a single optical path to pass through a sample of gas being analyzed to determine a concentration of at least one component of the gas;
    alternating between a first modulating and a second modulating of the beam of light passing through the sample of gas, wherein the first modulating comprises modulating the wavelength of the beam of light with a modulation signal having a modulation frequency at a first frequency value, and wherein the second modulating comprises modulating an intensity of the beam of light with a burst signal having a burst frequency at a frequency value different than the first frequency value, wherein an N-th harmonic of the burst frequency has a frequency value equal to a frequency value of an M-th harmonic of the modulation frequency, wherein N and M are respective positive integer numbers;
    disposing in the single optical path a detector to receive the beam of light having passed through the sample of gas and generating a detector output in response to the received beam of light, wherein the detector output comprises a first signal formed in response to the modulating of the wavelength of the beam of light with the modulation signal and further comprises a second signal formed in response to the modulating of the intensity of the beam of light with the burst signal; and
    processing the first and second signals and calculating a ratio of the first and second signals, the ratio being indicative of a concentration of said at least one component of the gas.

2. The method of claim 1, wherein N=7 and M=2.

3. The method of claim 1, wherein the modulation signal comprises a sinusoidal.

4. The method of claim 3, wherein the burst signal comprises a square wave.

5. The method of claim 3,
    wherein the sweep function comprises a sawtooth, and
    wherein the amplitude of the burst signal is different before and after the sweep.

6. The method of claim 1, wherein the burst signal comprises a square wave.

7. The method of claim 1 further comprising sampling the detector output at a sampling frequency selected so that the M-th harmonic of the modulation frequency and the N-th harmonic of the burst frequency is each folded to a common frequency value equal to the burst frequency based on an aliasing effect.

8. The method of claim 1, wherein the ratio of the first and second signals is free from an effect not related to the gas being analyzed, wherein said effect is defined by a product of $I_L \times T$, where $I_L$ represent the intensity of the light beam from the light source and T represents an optical transmission factor.

9. A wavelength modulation spectroscopy system, comprising:
    a wavelength frequency-tunable light source arranged to direct along a single optical path a beam of light to pass through a sample of gas being analyzed;
    a first modulator and second demodulator configured to alternatively modulate the beam of light passing through the sample of gas, wherein the first modulator is configured to modulate the wavelength of the beam of light with a modulation signal having a modulation frequency at a first frequency value, and the second demodulator is configured to modulate an intensity of the beam of light with a burst signal having a burst frequency at a frequency value different than the first frequency value, wherein an N-th harmonic of the burst frequency has a frequency value equal to a frequency value of an M-th harmonic of the modulation frequency;
    a detector disposed in the single optical path to receive the beam of light having passed through the sample of gas and generating a detector output in response to the received beam of light, wherein the detector output comprises a first signal formed in response to the modulating of the wavelength of the beam of light with the modulation signal and further comprises a second signal formed in response to the modulating of the intensity of the beam of light with the burst signal; and a signal processor configured to process the first and second signals and calculate a ratio of the first and second signals, the ratio being indicative of a concentration of said at least one component of the gas.

10. The system of claim 9, wherein N=7 and M=2.

11. The system of claim 9, wherein the modulation signal comprises a sinusoidal.

12. The system of claim 9, wherein the burst signal comprises a square wave.

13. The system of claim 9,
wherein the sweep function comprises a sawtooth, and
wherein the amplitude of the burst signal is different before and after the sweep.

14. The system of claim 9, further comprising an analog-to-digital converter configured to sample the detector output at a sampling frequency selected so that the M-th harmonic of the modulation frequency and the N-th harmonic of the burst frequency is each folded to a common frequency value equal to the burst frequency based on an aliasing effect.

15. The system of claim 14, wherein N=7 and M=2.

16. The system of claim 15, wherein the modulation signal comprises a sinusoidal.

17. The system of claim 16, wherein the burst signal comprises a square wave.

18. The system of claim 17,
wherein the sweep function comprises a sawtooth, and
wherein the amplitude of the burst signal is different before and after the sweep.

19. The system of claim 9, wherein the ratio of the first and second signals is free from an effect not related to the gas being analyzed, wherein said effect is defined by a product of $I_L \times T$, where $I_L$ represent the intensity of the light beam from the light source and T represents an optical transmission factor.

* * * * *